United States Patent [19]

Steen et al.

[11] Patent Number: 5,447,517

[45] Date of Patent: Sep. 5, 1995

[54] APPARATUS AND METHOD OF CALIBRATING A SURGICAL KNIFE

[75] Inventors: Mark E. Steen, Chino Hills; Ken T. Cheng, Irvine, both of Calif.

[73] Assignee: Keratron Group, Newport Beach, Calif.

[21] Appl. No.: 345,550

[22] Filed: Nov. 28, 1994

Related U.S. Application Data

[60] Continuation of Ser. No. 89,656, Jul. 9, 1993, abandoned, which is a division of Ser. No. 953,489, Sep. 29, 1992, Pat. No. 5,323,543.

[51] Int. Cl.$^6$ .............................................. A61B 17/32
[52] U.S. Cl. ...................................... 606/167; 606/166
[58] Field of Search ................. 606/166, 167, 170, 172

[56] References Cited

U.S. PATENT DOCUMENTS

| | | | |
|---|---|---|---|
| 4,499,898 | 2/1985 | Knepshield et al. | 606/166 |
| 4,665,914 | 5/1987 | Tanne | 606/166 |
| 4,681,123 | 7/1987 | Valtchev | 606/167 |
| 4,750,489 | 6/1988 | Berkman et al. | 606/166 |
| 4,768,509 | 9/1988 | Grosvenor et al. | 606/166 |
| 4,884,569 | 12/1989 | Fedorov et al. | 606/166 |

*Primary Examiner*—Stephen C. Pellegrino
*Assistant Examiner*—Michael Peffley
*Attorney, Agent, or Firm*—Blakely, Sokoloff, Taylor & Zafman

[57] ABSTRACT

An apparatus and method for zeroing, calibrating and setting a surgical knife. The surgical knife includes a blade that has a tip which can move relative to a footplate that extends from the body of the knife. The apparatus includes a calibration housing that is coupled to a surgical microscope. The calibration housing has a transparent sleeve coupled to a holder, which are both adapted to receive and support the surgical knife. The calibration housing is constructed so that the knife and sleeve are in the line of sight of the microscope. The knife typically has a sensor that can sense the position of the blade tip relative to the footplate. The sensor provides an output signal to a visual display which converts the signal to a visual readout. The visual display also has an input device that allows the surgeon to zero the visual display. To calibrate the knife, the surgeon inserts the knife into the calibration housing until the footplate is parallel with a marking on the sleeve. The surgeon then adjust the knife until the tip of the blade is parallel with the marking and the footplate. When the three members are parallel the surgeon "zeros" the visual display. Movement of the blade within the sleeve can also be used to calibrate the visual display and set the knife.

3 Claims, 6 Drawing Sheets

APPARATUS AND METHOD OF CALIBRATING A SURGICAL KNIFE

This is a continuation of application Ser. No. 08/089,656 filed Jul. 9, 1993, now abandoned which is a divisonal of application Ser. No. 07/953,489, filed Sep. 29, 1992, now U.S. Pat. No. 5,323.543.

BACKGROUND OF THE INVENTION

1. Field of the Invention

The present invention relates to an apparatus and method for zeroing, calibrating and setting a surgical knife.

2. Description of Related Art

There presently exist a surgical procedure for correcting defects in the human eye such as myopia and astigmatism, which is commonly known as radial keratotomy. Radial keratotomy includes cutting a series of radial, non-penetrating incisions on the outer periphery of the cornea. The incisions alter the shape of the cornea and correct the deficiencies in the eye.

The incisions are typically performed by a knife that is held and manipulated by the surgeon. Surgical knives used for radial keratotomy have a blade which can move relative to a footplate that extends from the body of the knife. The incisions are formed by placing the footplate on the surface of the cornea and moving the knife across a portion of the eye. The depth of the cut is therefore determined by the relative distance between the footplate and the tip of the blade.

The knife typically has a thimble that allow the surgeon to move the blade relative to the footplate. The length of the blade is set by rotating the knife a predetermined number of turns. A typical radial incision depth is between 580–620 microns with a required accuracy of plus or minus 5 microns. It is therefore important to establish a high degree of accuracy when setting the blade of the knife.

U.S. Pat. No. 4,750,489 issued to Berkman et al, discloses a surgical knife and a method for setting the blade relative to the footplate of the knife. Incorporated into the body of the Berkman knife is a linear variable differential transformer ("LVDT") which senses the position of the blade relative to the footplate. The LVDT is coupled to a visual display which provides a readout that indicates the distance between the tip of the blade and the footplate.

To obtain an accurate readout, the blade must be initially aligned or "zeroed" with the footplate. Zeroing the Berkman system is performed by inserting the knife into a zeroing sleeve. The zeroing sleeve has a reflective membrane that reflects a pattern of light to a plurality of light sensors. The knife is inserted into the sleeve until the footplate is in contact with the reflective membrane. The knife is then adjusted until the blade advances to a point where the tip deflects the reflective membrane. Deflection of the membrane disturbs the light pattern which is sensed by the sensors and interpreted by the visual display as the zero position of the blade. The Berkman system for calibrating the knife has been found to be somewhat unreliable to use and expensive to produce.

U.S. Pat. No. 4,662,075 issued to Mastel et al, discloses another method of zeroing and setting a surgical knife that uses an apparatus typically referred to as a micron table. The micron table has a microscope coupled to an X-Y table. The lens of the microscope has a cross shaped reticle which provides a pair of reference lines for the user. The knife is placed on the X-Y table and the table is adjusted until the footplate and blade are centered within the reticle. The knife thimble is then rotated until the tip of the blade is zeroed with the footplate of the knife. After the blade is zeroed, the X-Y table is adjusted to move the footplate and blade a predetermined distance from the center of the reticle. The knife thimble is again rotated so that the blade is moved back to the center of the reticle. The knife is then transferred to a sterile operating field.

During the transportation of the knife, the tip may move to a different location, resulting in an inaccurate blade setting. When this occurs the knife must be returned to the micron table and reset. Additionally, while performing surgery it may become apparent to the surgeon that the blade setting is either too short or too long. Resetting the knife again requires a trip back to the micron table. The micron table is typically located separate from the operating field, wherein the knife may require resterilization every time the knife is calibrated and set. Such a procedure wastes valuable operating time. It would therefore be desirable to have a system for accurately zeroing and setting a surgical knife at the operating site.

SUMMARY OF THE INVENTION

The present invention is an apparatus and method for zeroing, calibrating and setting a surgical knife. The surgical knife includes a blade that has a tip which can move relative to a footplate that extends from the body of the knife. The knife also has a thimble which allows a surgeon to move the blade relative to the footplate. The blade is preferably coupled to the thimble by differential threads which provide small increments of translational movement in response to relatively large angular displacements of the thimble. The differential threads also prevent the blade from drifting after the tip is set. The apparatus includes a calibration housing that is coupled to a surgical microscope typically used to perform a surgical procedure such as radial keratotomy. The calibration housing has a transparent sleeve coupled to a holder, which are both adapted to receive and support the surgical knife. The sleeve is preferably flat to reduce the parallax of the optical system.

The knife is inserted into the calibration housing until the footplate is parallel with a first marking on the sleeve. The calibration housing is constructed so that the knife and sleeve are in the line of sight of the microscope The present invention therefore allows the surgeon to accurately view the footplate, blade tip and the first marking of the sleeve.

The knife typically has a sensor that can sense the position of the blade tip relative to the footplate. The sensor sends an output signal to a visual display which converts the signal to a visual readout. The readout provides the distance between the tip of the blade and the footplate. The visual display also has an input device that allows the surgeon to zero the visual display.

To calibrate the knife, the surgeon inserts the knife into the calibration housing until the footplate is parallel with the first marking on the sleeve. The surgeon then adjust the knife until the tip of the blade is parallel with the first marking and the footplate. When the three members are parallel the surgeon "zeroes" the visual display. The sleeve may also have a second marking located a predetermined distance from the first marking. The accuracy of the visual display can be determined by moving the tip of the blade to the second marking and then looking at the readout to see if the display is providing the correct value.

The blade of the knife can be set by rotating the thimble and moving the tip until the visual readout provides the desired value. The sleeve may also have a scale to provide a visual indication of the distance between the tip of the blade and the footplate of the knife. The scale can be used with or without the sensor and visual display. The calibration housing is pivotally connected to the microscope, so that the surgeon can remove the knife, move the housing out of the line of sight and begin the surgical procedure.

Therefore it is an object of the present invention to provide a system for accurately zeroing a surgical knife at the operating site.

It is also an object of the present invention to provide a system for accurately calibrating a surgical knife at the operating site.

It is also an object of the present invention to provide a system that allows the surgeon to visually set the blade length of a surgical knife at the operating site.

It is also an object of the present invention to provide a surgical knife that can be accurately set and has a blade that does not drift.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 4a is an enlarged top view showing a scale formed in the sleeve of FIG. 4;

FIG. 5b is a side view of FIG. 4a;

FIG. 11 is a perspective view of an alternate embodiment of the calibration housing showing a gear assembly that can move the blade of the knife;

FIG. 13 is a side view of an alternate embodiment of the system;

FIG. 15 is a side view of an alternate embodiment of the knife of FIG. 14.

DETAILED DESCRIPTION OF THE INVENTION

Figure 1:
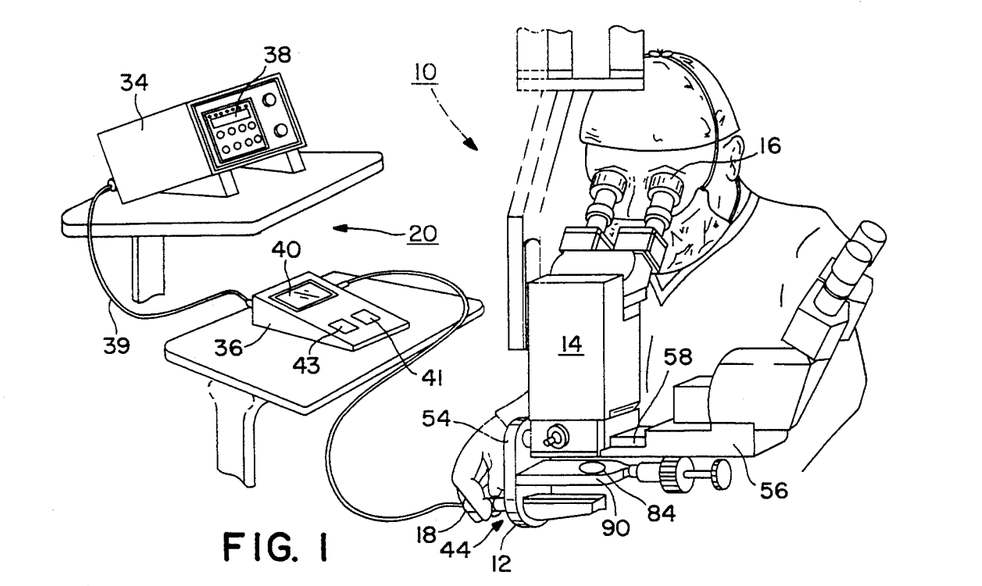
FIG. 1 is a perspective view of a system of the present invention.

Referring to the drawings more particularly by reference numbers, FIG. 1 shows a system 10 of the present invention. The system 10 is used to zero, calibrate and set a surgical knife. The knife is typically used to perform surgical procedures such as radial keratotomy, although it is to be understood that the knife and system can be used for other surgical procedures. The system 10 is located in a sterile environment, preferably at the operating site. It is to be understood that one of the main advantages of the present system is the ability of the surgeon to zero, calibrate and set the knife in a sterile room and at the site of the surgery. Although the system is described as being operated by a surgeon, it is to be understood that the present invention may be practiced by other qualified personnel such as a nurse.

In the preferred embodiment, the system 10 has a calibration housing 12 coupled to a microscope 14. The microscope 14 has a pair of eyepieces 16 that allow the surgeon to view magnified objects as is known in the art. The microscope 14 is typically suspended from the ceiling and located above the operating table. The system 10 also includes a surgical knife 18 that is connected to a visual display system 20.

Figure 2:
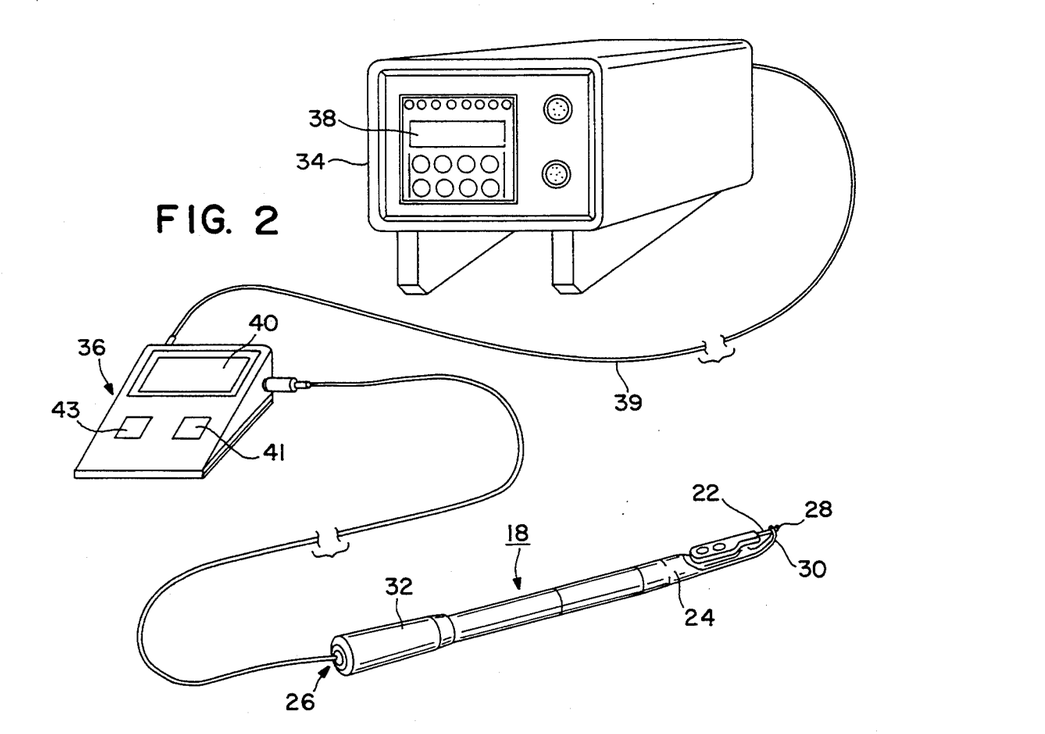
FIG. 2 is a perspective view of a surgical knife connected to a visual display system.

As shown in FIG. 2, the surgical knife 18 has a blade 22 that can move relative to the body 24 of the knife 18. The knife 18 includes a sensor 26 that can determine the relative position of the blade tip 28 to a footplate 30 which extends from an end of the body 24. The knife has a thimble 32 coupled to the blade 22. Rotation of the thimble 32 moves the blade 22 relative to the footplate 30. The thimble 32 allows the surgeon to manually adjust the blade 22 of the knife.

The sensor 26 provides an output signal to the visual display system 20, which receives the output signal and provides a readout that indicates the distance from the blade tip 28 to the footplate 30. The visual display system 20 may include a main display unit 34 and a remote display unit 36. The main unit 34 typically contains the electronic hardware of the display system 20 and a main readout display 38 that provides the distance between the tip of the blade and the footplate 30. The remote unit 36 is connected to the main unit 34 through a cable 39 which allows the unit 36 to be in close proximity to the surgeon. The remote unit 36 has a remote readout display 40 that provides the same blade distance readout as the main unit 34. The visual display system 20 also has a control button 41 which allows the surgeon to set the visual display to zero. The control button 41 is preferably located on the remote unit 36, but may also be positioned near the microscope 14 and calibration housing 12.

Figure 3:
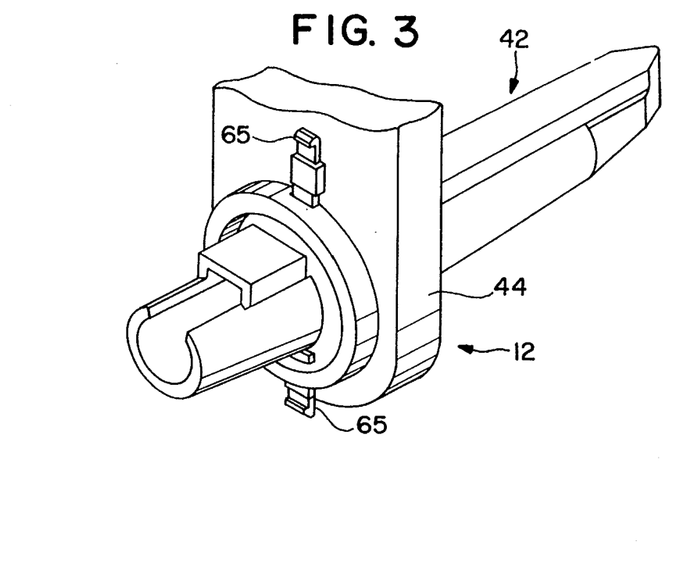
FIG. 3 is a perspective view of a calibration housing of the system.
Figure 4:
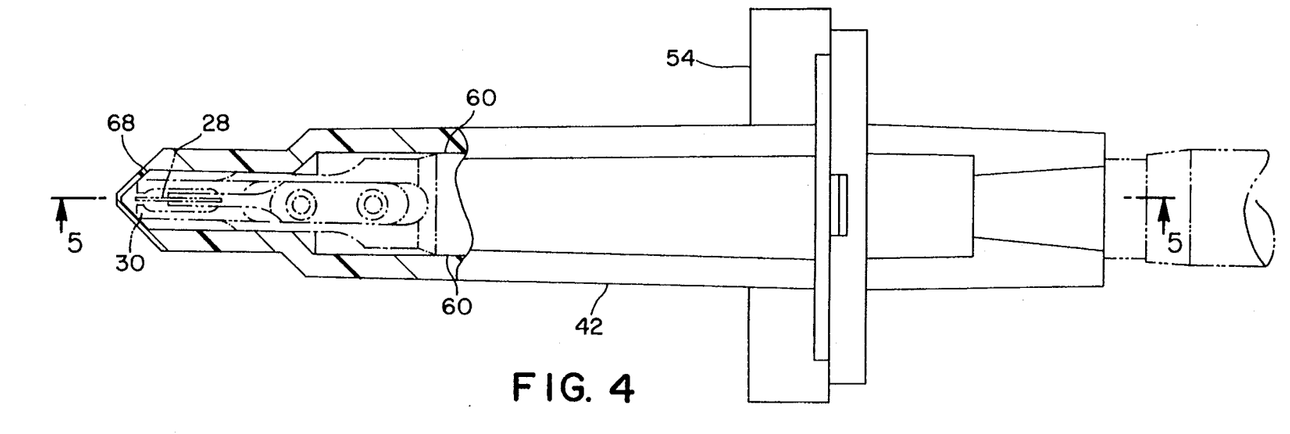
FIG. 4 is a top view of a knife inserted into the calibration housing.
Figures 4A, 5B, 11, 13, 15:
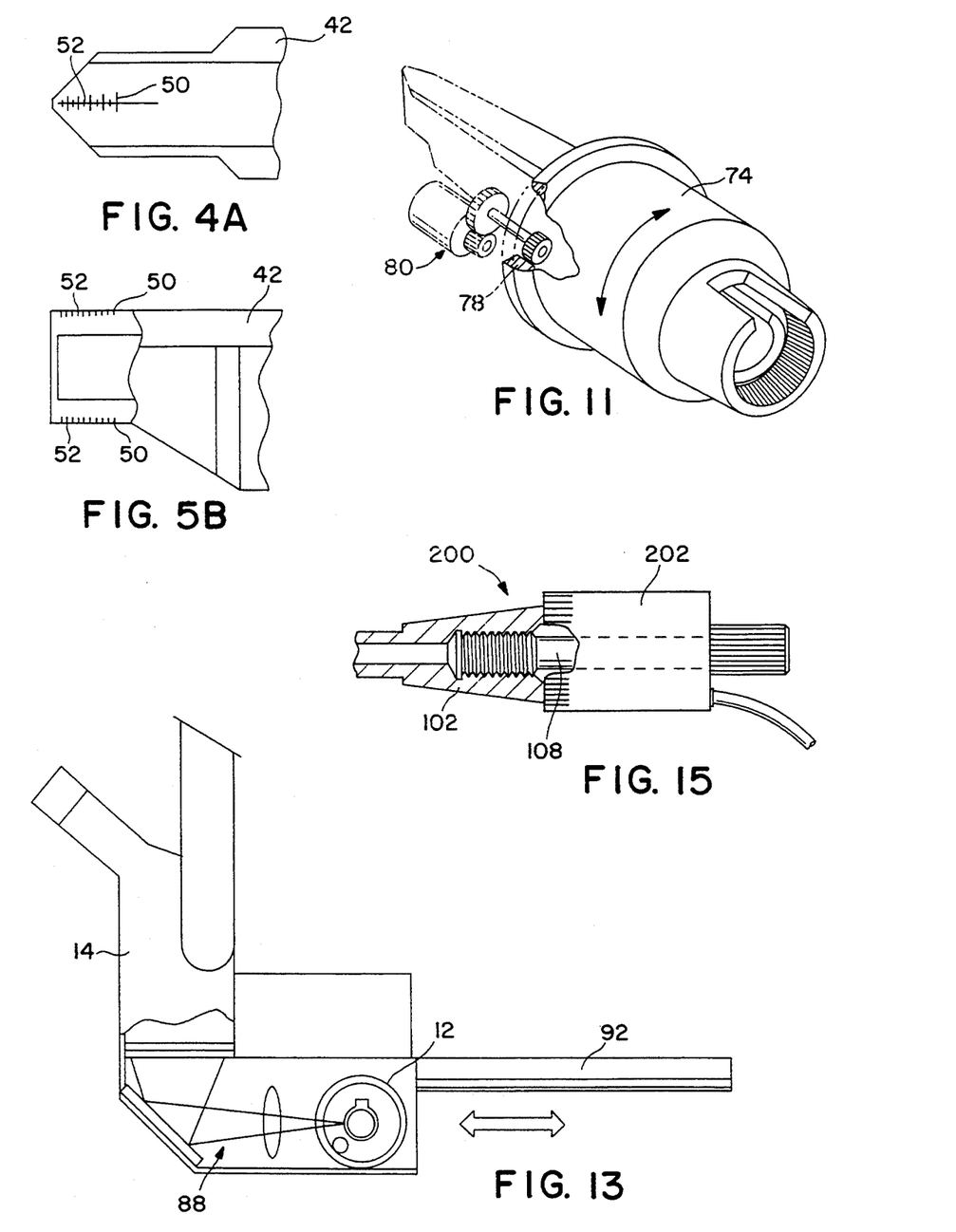

FIG. 3 shows a calibration housing 12 which includes a first sleeve 42 coupled to a holder 44. The holder 44 has a first inner cavity that allows the knife 18 to extend therethrough. The sleeve 42 has a second inner cavity 48 that generally conforms to the outline of the knife 18. As shown in FIGS. 4a and 5b, the sleeve 42 has a first marking 50 that provides a reference point and at least one second marking 52 located a predetermined distance from the first marking 50. The sleeve 42 may also have additional markings to create a scale. The sleeve 52 is preferably constructed entirely from a transparent plastic such as acrylic.

As shown in FIG. 1, the calibration housing 12 is attached to an arm 54 that is connected the microscope 14. The arm 54 is typically an extension of the holder 44. The arm 54 and calibration housing 12 are constructed so that the sleeve 42 is in the line of sight with the microscope 14, when the arm 54 is in the "extended" position. This position allows the surgeon to accurately view the sleeve 42 and the blade 22 of the knife. The arm 54 is adapted to move the sleeve 42 out of the line of sight of the microscope 14, when the calibration housing 12 is moved into a retracted position. The arm 54 may have detents (not shown) to lock the arm 54 into the extended and retracted positions.

Figure 5:
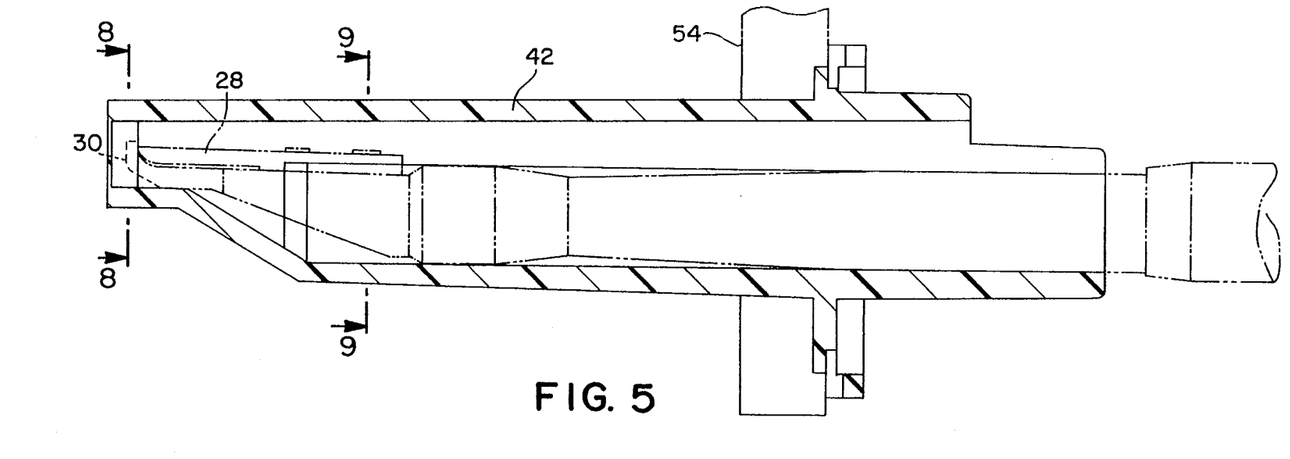
FIG. 5 is a cross-sectional view taken at line 5—5 of FIG. 4.
Figures 6, 7:
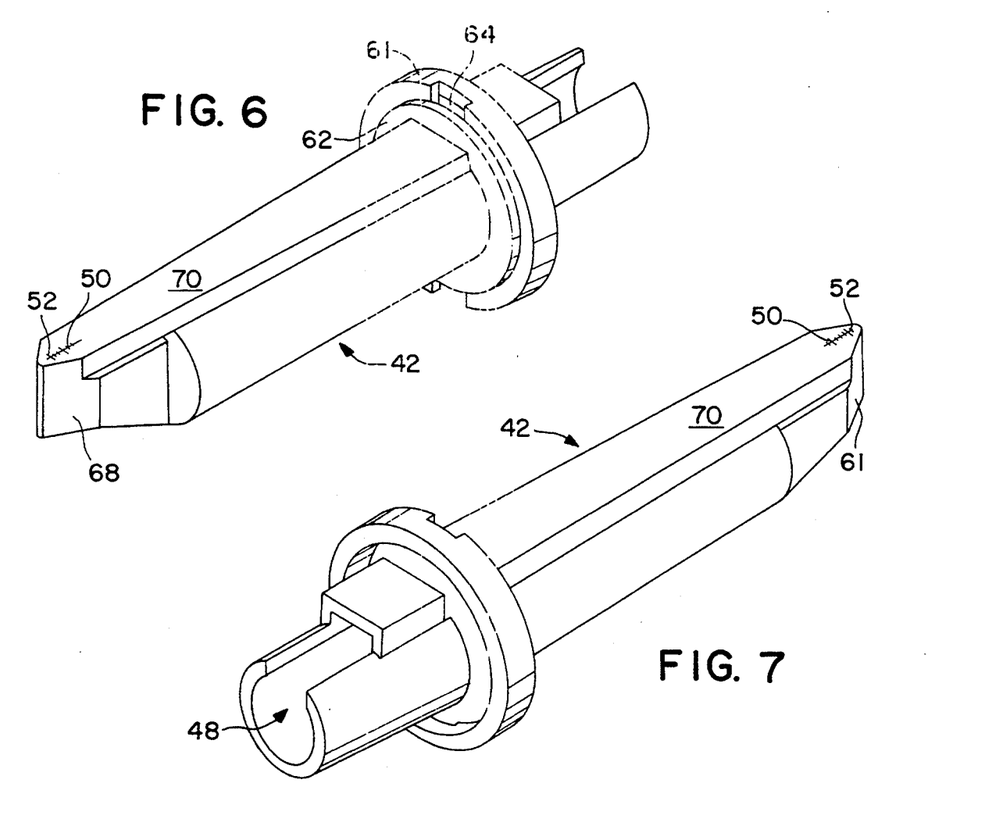
FIG. 6 is front perspective view of a calibration sleeve.
FIG. 7 is a rear perspective view of the sleeve of FIG. 6.
Figure 8:
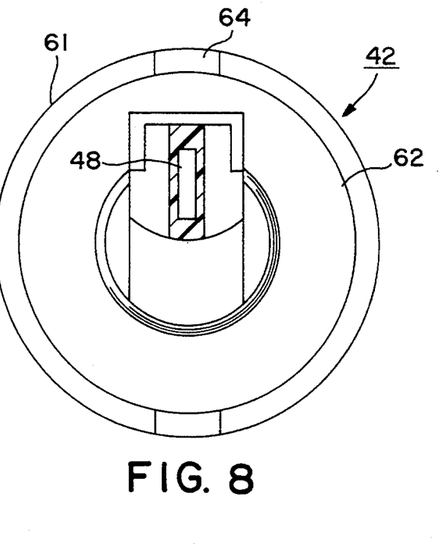
FIG. 8 is a cross-sectional view taken at line 8—8 of FIG. 4.
Figure 9:
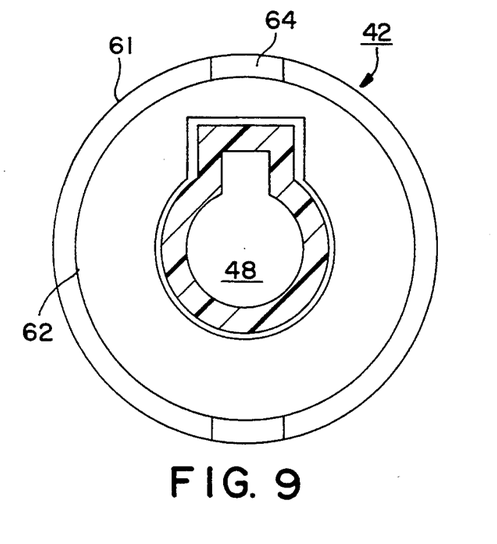
FIG. 9 is a cross-sectional view of taken at line 9—9 of FIG. 4.

To calibrate the surgical knife 18, the arm 54 is moved into an extended set position and the knife 18 is inserted into the calibration housing 12. As shown in FIGS. 4 and 5, the knife 18 is inserted into the housing 12 until the footplate 30 is parallel with the first marking 50. The sleeve 42 has clamping walls 60 that capture the body 24 and hold the same in place. The tolerances between the clamping area 60 and the first marking 50 are minimal, so that the footplate 30 is aligned with the marking 50 when the knife is fully inserted into the housing 12.

The surgeon then rotates the thimble 32 of the knife and moves the blade 22 until the tip 28 is parallel with the first marking 50 and the footplate 30. Once the blade tip 28 is zeroed, the surgeon pushes the control button 41 and zeros the visual display. After the blade tip 28 is zeroed, the surgeon may remove the knife 18 and set the blade 22, by turning the thimble 32 until the readout indicates that the tip 28 has reached the desired distance from the footplate 30. Alternately, the surgeon may set the knife 18 within the calibration housing 12 and visually verify the blade length with the scale on the sleeve 42. It is to be understood that the scale can be used to set a knife that does not have a sensor 26 and a visual display system 20.

After zeroing the blade tip, the surgeon can determine the accuracy of the knife sensor 26 and visual display system 20 by moving the blade tip 22 from the first marking 50 to the second marking 52 and viewing the readout display. The readout should correlate to the distance between the first and second markings. For example, if the distance between markings is 200 microns, the visual display should read 200 microns when the blade is moved to the second marking. A different readout provides an indication to the surgeon that the sensor and/or visual display system is in error. The display system 20 may have a second calibration button 43 which allows the surgeon to recalibrate the knife sensor 26. In the example above, if the display does not readout "200", the surgeon depresses the second button 43. The system 20 is then recalibrated so that movement of the blade will be accurately represented by the system.

FIGS. 6-9 show a preferred embodiment of the sleeve 42. The sleeve 42 has a first annular flange 61 that is adapted to come into contact with the holder 44. The sleeve 42 also has a second annular flange 62 that is received by an annular groove (not shown) in the holder 44. The flange 62 and groove are constructed to align the sleeve 42 with the holder 44 and prevent relative movement between the members. The sleeve 42 also has a pair of slots 64 that are adapted to receive a pair of keys 65 that extend from the holder 44. The keys 65 are adapted to slide into the slots 64 and attach the sleeve 42 to the holder 44. The key/slot arrangement also prevents relative rotation between the two members.

The portion of the sleeve 42 containing the markings 50 and 52 preferably has a rectangular cross-section. Such a construction provides a flat surface which is in line with the microscope. The flat surface greatly reduces any parallax in the optical system. The sleeve 42 also has a pair of oblique walls 68 that provide a stop for the footplate 30 of the knife 18. The oblique walls 68 also capture the footplate 30 and prevent the knife from rotating relative to the sleeve 42. As an alternate embodiment, the markings 50 and 52 may be located on the oblique walls 68 and the sleeve 42 may be rotated 90° relative to the holder 44 shown in FIG. 3. The markings on the oblique walls appear to the viewer to be closer together than the actual distance that separates the lines. Such an arrangement may decrease the cost of manufacturing the sleeve and/or reduce the scale of the reticle. As a further alternative, the sleeve 42 could be constructed to have a circular cross-section, wherein the markings 50 and 52 are a plurality of annular rings extending around the circumference of the sleeve 42.

As shown in FIG. 5b, each marking preferably has a companion marking located on the opposite side of the sleeve 42. The dual markings allow the surgeon to determine when the microscope 14 is perpendicular with the marking in interest. For example, when zeroing the knife 18, the surgeon should only see the first marking 50 on the top surface 70 of the sleeve 42. If the bottom first marking is visible, then the microscope is not perpendicular with the sleeve 42. The microscope 14 is typically initially assembled so that first and second markings are aligned.

Figure 10:
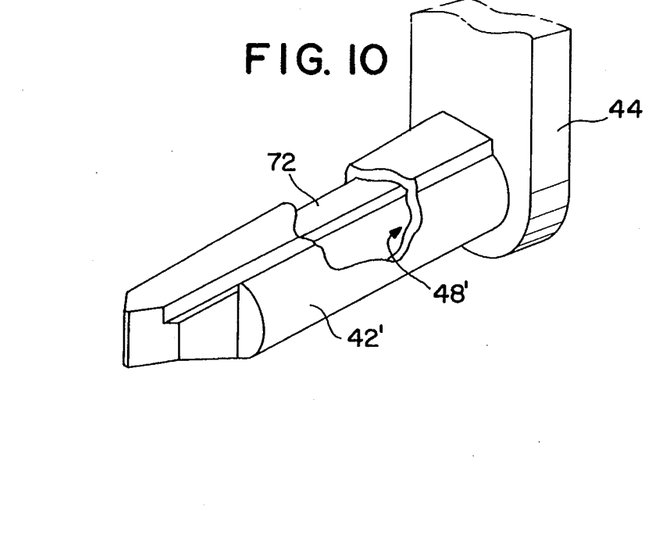
FIG. 10 is a perspective view of an alternate embodiment of the calibration housing showing a second sleeve within a first sleeve.

FIG. 10 shows an alternate embodiment of the calibration housing wherein a second sleeve 72 is inserted into the inner cavity 48' of a first sleeve 42'. The second sleeve 72 prevents the first sleeve 42' from coming in contacting with and possibly contaminating the blade 22 of the knife. The second sleeve 72 is typically replaced after each surgical procedure. Incorporation of the second sleeve 72 is particularly useful when it is not cost effective to continuously replace the first sleeve 42 and the fine markings.

FIG. 11 shows another alternate feature of the present invention. The assembly may include an additional sleeve 74 that moves the blade of the knife. The sleeve 74 may have a first set of internal teeth 76 that are coupled to external teeth (not shown) on the knife thimble 32, and a second set of internal teeth 78 that are coupled to a motor/gear assembly 80. The second teeth 78 and gear assembly 80 are preferably arranged as an eccentric gear assembly with the gear assembly containing the planetary gear. In operation, the motor/gear assembly rotates the sleeve 74, which rotates the thimble 32 and moves the blade 28. The electric motor may be connected to a computer which automatically moves and sets the blade of the knife. The depth of the incision during a radial keratotomy procedure is determined by the thickness of the cornea. The cornea is typically measured by a pachymeter which can store the dimensions in a data base. The computer can then utilize the measurements to automatically drive the motor/gear assembly 80 and set the blade length of the knife.

Figure 12:
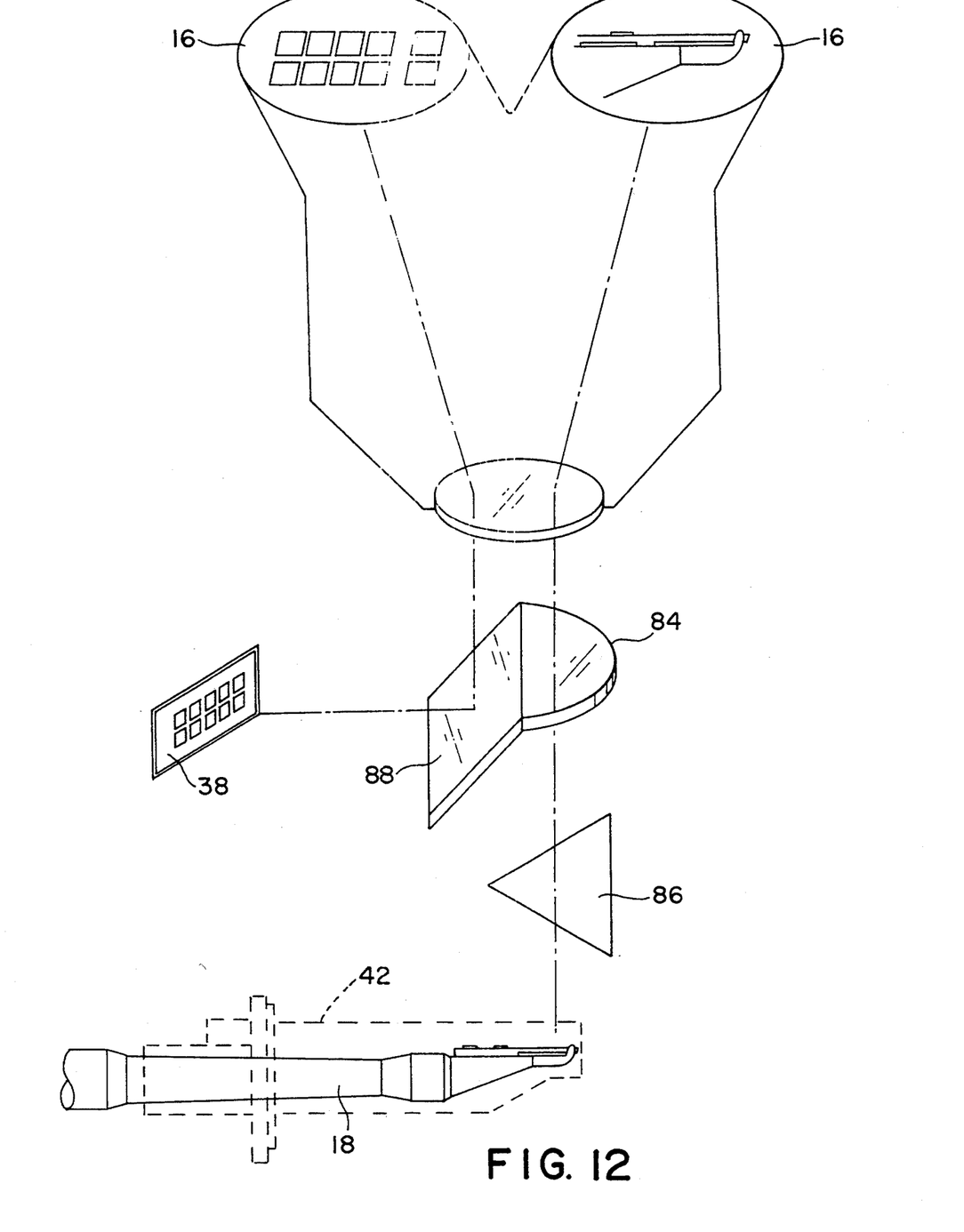
FIG. 12 is a schematic of an optical system of the present invention.

FIG. 12 shows an optical system of the present invention. During eye surgery, the microscope 14 is typically set to magnify an object between 18X-20X. Calibrating and setting the knife typically requires a larger magnification. To increase the power of the optical system, a focusing lens system 84 is inserted between the microscope and the sleeve 42. The lens system 84 is preferably constructed to increase the power of the optical system in the range of 50X–100X. The lens system 84 allows the surgeon to accurately view the relationship between the blade tip and the fine markings on the sleeve. Between the lens system 84 and the sleeve 42 is a prism 86 or other refraction device for bending the light directly into one of the eyepieces. To reduce parallax, the other eye piece is directed to another object by a mirror 88. The other object is preferably the readout display 38 of the visual display system. The dual optic system allows the surgeon to view the blade 22 and sleeve 42 with one eye and look at the visual readout with the other eye, without leaving the microscope 14. As shown in FIG. 1, the lens system 84, prism 86 and mirror 88 are preferably attached to a plate 90 that extends from the arm 54. In the preferred embodiment, a light source is located beneath the sleeve 42 opposite the lens system 84 to fully illuminate the knife 18 and sleeve 42. The light source may include a filter that will only allow a predetermined wavelength(s) of light to be directed onto the sleeve 42. In the preferred embodiment, the sleeve 42 is illuminated with either amber or green light.

As an alternate embodiment, the optical system can be constructed without the mirror 88, wherein the light is bent directly into both eyepieces. Light from the readout display can be directed into the eyepieces so that the surgeon can see the readout while viewing the blade and sleeve. Such an optical system is commonly referred to as a "heads up" display.

FIG. 13 shows another alternate embodiment, wherein the calibration housing 12 and lens system 84 can move along a "dove tail" table 92 between the retracted and extended positions.

Figure 14:
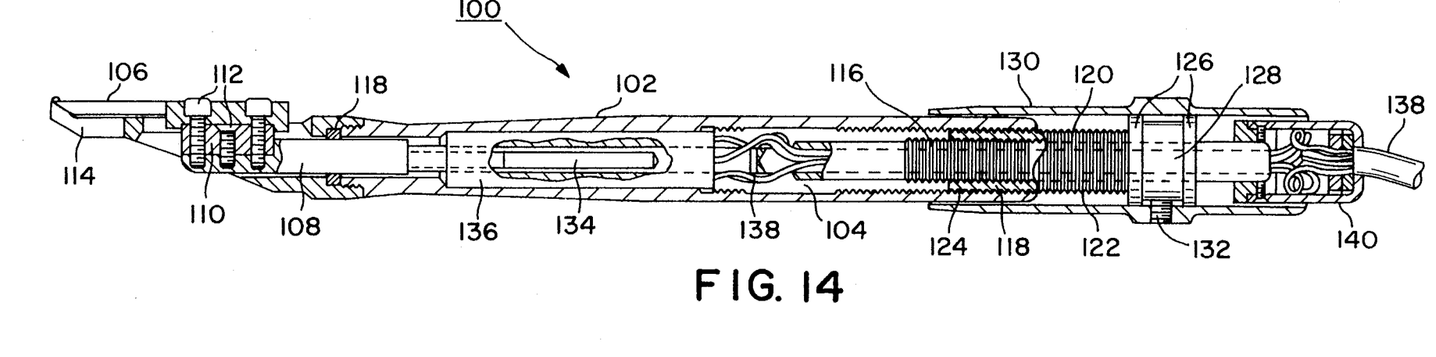
FIG. 14 is a cross-sectional view of a knife.

FIG. 14 shows a preferred embodiment of a knife 100. The knife 100 has a body 102 which has an inner cavity 104. The knife 100 also has a blade 106 that is attached to a first shaft 108 by a coupling block 110 and a plurality of screws 112. The blade 106 can move relative to a footplate 114 that extends from a footplate housing 116 which screws onto the end of the body 102 of the knife. The housing 116 may contain a bearing 118 which supports and aligns the shaft 108.

The first shaft 108 has a threaded portion 116 that engages an internal thread 118 of a second shaft 120. The second shaft 120 has an external thread 122 that engages an internal thread 124 of the body 102. The second shaft 120 also has a pair of annular flanges 126 separated by a collar 128. The second shaft 120 is coupled to a thimble 130 by a set screws 132 which engage the collar 128.

The blade 106 can be moved by rotating the thimble 130. Rotation of the thimble 130 rotates the second shaft 120 relative to the body 102 and the first shaft 108 relative to the second shaft 120. The translation of the shafts 108 and 120 are in opposite direction such that the actual movement of the blade 106 is equal to the difference in the movements of the shafts. The differential movement of the shafts allows the user to induce small increment movements of the blade 106 with relatively large angular displacements of the thimble 130. Such a relationship allows the user to more accurately move the blade in the small increments typically required to calibrate and set the knife. In the preferred embodiment, the turn ratio of the threads 122/124 to the threads 116/118 is proportioned to allow a blade extension of between 100–500 microns for each thimble revolution. The opposing motion of the shafts insures constant contact between the threads of the first shaft 108 and the internal threads of the second shaft 120, thereby preventing "float" in the blade. The thimble 130 typically has a scale (not shown) on the outer surface that provides an indication of the relative distance between the blade 106 and footplate 114.

The shaft 108 has a magnetic core 134 that is coupled to a transformer sleeve 136. The transformer sleeve 136 is coupled to the visual display system 20 by wires 138 that extend through the knife 100. The wires 138 are typically introduced through an end cap 140 that is attached to the second shaft 120. The sleeve 136 typically contains three coils which together with the magnetic core 134 comprise a linear variable differential transformer ("LVDT"). Such a sleeve is sold by Lucas Schaevitz under the designation "MP Series". The LVDT is an electromechanical device that produces an electrical output that is linearly proportional to the linear displacement of the magnetic core 134. Use of an LVDT in a surgical knife is disclosed in U.S. Pat. No. 4,750,489 issued to Berkman, et al, which is hereby incorporated by reference.

The coils of the sleeve 136 are connected to the main display unit 20 which receives the electrical output of the LVDT and converts the signal into a visual alphanumeric display. The unit also has the buttons 41 and 43 which allows the user to zero and recalibrate the display, respectively. Such a unit is also sold by Lucas Schaevitz under the "MP Series" designation. Although an LVDT and display unit are shown and described, it is to be understood that the knife can be zeroed and set without the LVDT or display unit by using the markings on the sleeve 42.

FIG. 15 shows an alternate embodiment of the knife. Instead of the LVDT, the knife 200 may contain an optical encoder 202. The optical encoder 202 typically has a plurality of markings coupled to the shaft 108 and an optical sensor unit attached to the body 102 of the knife. The optical encoder 202 produces an electrical output that corresponds to the rotational movement of the shaft 108. The electrical output of the encoder 202 is interpreted by the visual display system 20 to produce a visual alphanumeric display, which corresponds to the distance between the tip of the blade and the footplate of the knife. An optical encoder that provides an output in response to rotational movement is sold by Hewlett-Packard under the designations HEDS 5500/5540 and 5600/5640.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A surgical knife, comprising:
   a body having an inner cavity that has an internal threaded portion, said body further having a footplate at a first end of said body;
   a first gear that has a threaded bore and an external thread that engages said internal thread of said body and moves relative to said body;
   a blade with a tip that is adjacent to said footplate, said blade being coupled to said first gear by a threaded shank that engages said threaded bore such that said shank moves in a direction opposite from said first gear; and, a thimble attached to said first gear such that rotation of said thimble rotates said first gear and translates said blade relative to said footplate, wherein said blade translation relative to said footplate is a result of a differential movement between said first gear and said shank.

2. The surgical knife as recited in claim 1, wherein said blade has a magnetic core member that moves with said shank relative to said body.

3. The surgical knife as recited in claim 2, further comprising coil means coupled to said magnetic core member for sensing the position of said blade tip relative to said footplate.

* * * * *